(12) United States Patent
Nemir et al.

(10) Patent No.: US 6,843,766 B1
(45) Date of Patent: Jan. 18, 2005

(54) FECAL INCONTINENCE MANAGEMENT DEVICE

(75) Inventors: David C. Nemir, El Paso, TX (US); Edward Rubio, El Paso, TX (US)

(73) Assignee: X-L Synergy, El Paso, TX (US)

( * ) Notice: Subject to any disclaimer, the term of this patent is extended or adjusted under 35 U.S.C. 154(b) by 0 days.

(21) Appl. No.: 10/401,479

(22) Filed: Mar. 28, 2003

Related U.S. Application Data

(60) Provisional application No. 60/435,808, filed on Dec. 21, 2002.

(51) Int. Cl.⁷ .............................................. A61F 2/02
(52) U.S. Cl. ......................................................... 600/31
(58) Field of Search .................. 600/29, 587, 591, 600/547, 373, 506, 561, 488, 593, 560, 55.1, 325, 546; 482/8, 112, 113; 606/192, 591; 73/379.01; 607/39, 138, 116; 250/341.8, 341.2; 604/93.01, 110, 111, 544

(56) References Cited

U.S. PATENT DOCUMENTS

| | | | |
|---|---|---|---|
| 4,197,458 A | * | 4/1980 | Perren .................... 250/341.2 |
| 4,380,237 A | * | 4/1983 | Newbower ................ 600/506 |
| 4,686,985 A | | 8/1987 | Lottick |
| 4,813,422 A | | 3/1989 | Fisher et al. |
| 4,873,990 A | * | 10/1989 | Holmes et al. ............. 600/561 |
| 4,909,263 A | * | 3/1990 | Norris ........................ 607/39 |
| 4,979,947 A | | 12/1990 | Berman |
| 5,005,586 A | * | 4/1991 | Lahr ........................ 600/587 |
| 5,335,668 A | * | 8/1994 | Nardella .................... 600/547 |
| 5,533,515 A | * | 7/1996 | Coller et al. ............... 600/593 |
| 5,674,238 A | * | 10/1997 | Sample et al. ............. 606/192 |
| 5,695,484 A | | 12/1997 | Cox |
| 5,833,625 A | * | 11/1998 | Essen-Moller ............. 600/547 |
| 5,924,984 A | * | 7/1999 | Rao ........................... 600/373 |
| 6,096,057 A | | 8/2000 | Klingenstein |
| 6,217,529 B1 | * | 4/2001 | Wax et al. .................. 600/591 |
| 6,625,495 B1 | * | 9/2003 | Alon et al. ................. 607/116 |
| 2003/0176761 A1 | * | 9/2003 | Brady ......................... 600/29 |

* cited by examiner

*Primary Examiner*—Samuel G. Gilbert
*Assistant Examiner*—Nikita R. Veniaminov

(57) ABSTRACT

An apparatus, and corresponding method, for management of fecal incontinence comprising a catheter having at least two electrodes and an inflatable balloon, a non-conductive sleeve surrounding the electrodes, and an alarm box, wherein the catheter is insertable into a rectal vault and is inflatable to serve as a block to passage of stool and wherein moisture sensed by the electrodes triggers the alarm box and thereby notifies a user that fecal material has entered the rectal vault.

26 Claims, 3 Drawing Sheets

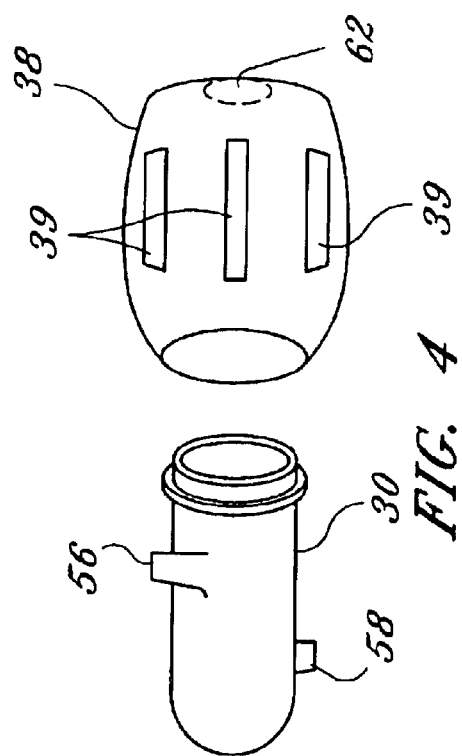
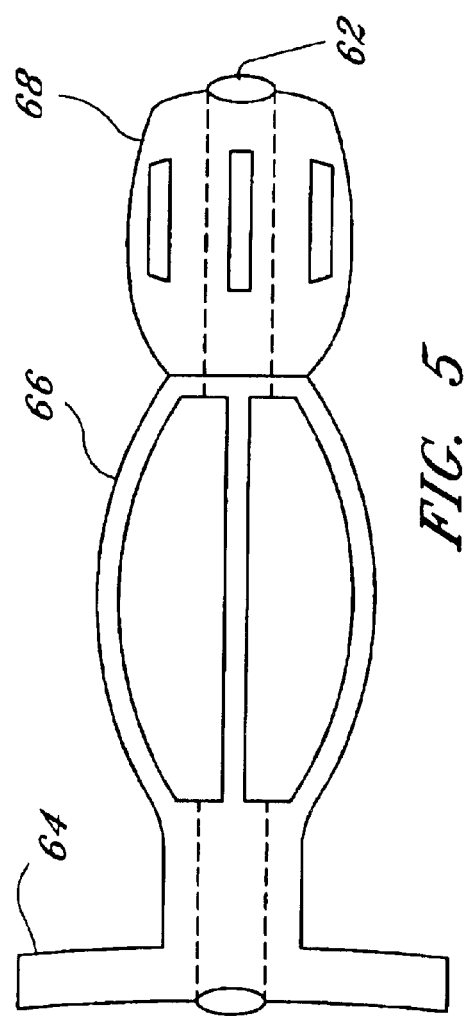
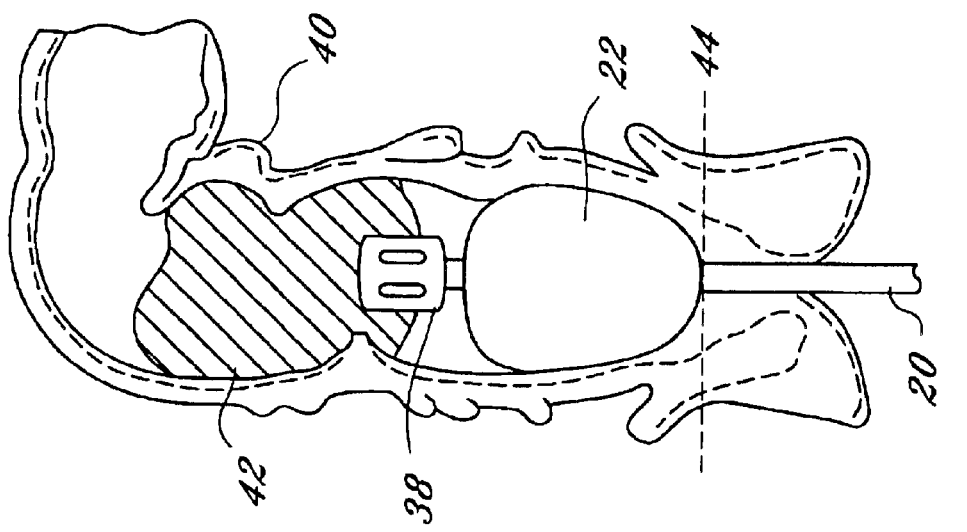

FECAL INCONTINENCE MANAGEMENT DEVICE

CROSS-REFERENCE TO RELATED APPLICATIONS

This application claims the benefit of the filing of U.S. Provisional Patent Application Ser. No. 60/435,808 entitled "Fecal Incontinence Management Device", to Nemir et al., filed on Dec. 21, 2002, and the specification therein is incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

This invention relates to an apparatus and method for the treatment of fecal incontinence wherein a fecal dam and fecal matter sensor are retained within the rectal vault to both prevent the passage of stool and to sense the occurrence of the filling of the rectal vault. When the sensor detects the presence of feces within the rectal vault, it signals the user or caregiver, allowing bowel management without the attendant need for diapers.

2. Description of Related Art

Fecal incontinence (FI) is the impaired ability to control stool. Although not a life-threatening disease, symptoms are often distressing and socially incapacitating. For patients who are under nursing care, there is a labor cost associated with disposing of fecal waste after a patient's incontinent episode and cleaning the patient after the event. Other problems include the possible excoriation of the patient's skin when it is exposed to fecal waste for significant amounts of time, and the risk of contamination for patients and nursing personnel from fecal material. Economically, the replacement of soiled bed linens, blankets and gowns compounds the loss of valuable nursing time and effort.

According to published reports, daily or weekly episodes of fecal incontinence occur in approximately 2% of the adult population and in about 7% of healthy, independent adults over the age of 65. Fecal incontinence is second only to dementia as the cause of institutionalization in the elderly and has been variously estimated to affect between 32% to 47% of all nursing home residents. In addition, FI accounts for expenses of over $400 million per year for adult diapers alone. The condition arises from a number of causes including spinal bifida, dementia, obstetric injury and side effects of anorectal surgery.

Minor degrees of fecal incontinence can be managed through diet. For some patients, surgery and/or biofeedback treatment has been used with success. For some patients, electrical stimulation may be used or an artificial sphincter may be surgically implanted. However, there are a large number of patients suffering from fecal incontinence for whom medical therapy and/or surgical therapy have either failed or are inappropriate due to the patient's medical condition, circumstances, or personal choice.

U.S. Pat. No. 4,686,985 (Lottick) discloses an anal dilator and occluder which has multiple chambers and which is inserted partially into the rectum and inflated, thereby serving a dual role of creating a controllable opening that can either block the passage of stool, or can be used to widen a narrow anus, allowing stool to pass. U.S. Pat. No. 4,979,947 (Berman) discloses an encapsulated expanding device that is coated in a gelatin capsule and is inserted into the rectum. When the gelatin capsule becomes moist, it dissolves, allowing a compressed foam to expand, thereby blocking the passage of stool. An attached string which comes out of a hole in the abdominal wall can then be used to adjust the position of the foam dam and allow feces to pass. The above two inventions do not disclose a means to alert the user as to the need to void the bowels. Since many patients suffer from nerve damage and cannot sense the need to evacuate the bowels, leakage or other undesirable effects may occur due to a prolonged retention of stool within the rectal vault.

U.S. Pat. No. 5,695,484 (Cox) discloses an adhesive patch for managing fecal incontinence by blocking seepage from the anus. U.S. Pat. No. 6,096,057 (Klingenstein) discloses a fecal incontinence device that uses external wings that are held in place in the cleft of the buttocks by an expandible member that is inserted into the rectum, with the combination said to block the passage of feces. The problem with these approaches is that they do not incorporate an alarming means to alert the user of the need to evacuate the bowels. Left unattended, the devices can lead to impaction of stool and attendant problems such as necrosis of tissues in the anus and rectum.

U.S. Pat. No. 4,813,422 (Fisher et al) discloses a bowel control probe apparatus and method for sensing and preventing incontinent episodes. A deflated balloon catheter is inserted into the rectal vault and is then inflated to serve as a dam to block the passage of stool. At the tip of the catheter assembly is an optical sensor that uses infrared technology to sense the presence of stool. When fecal matter presses into an optical emitter/detector sensor, it causes an alarm to alert the wearer or caregiver that the bowels need attention. One disadvantage of the device is that because fecal matter can cause permanent occlusion of the optical sensor, the device must be discarded after each use. For a patient who has multiple daily bowel movements, the cost can be prohibitive.

U.S. Provisional Patent Application Ser. No. 60/313,540 (Brady) proposes a bowel incontinence treatment device having a balloon catheter and annular electrode sensors to detect the presence of fecal material. The problem with the design is that annular electrodes are prone to nuisance tripping (false positives) upon insertion and during wear.

The present invention solves the problems of the prior art noted above.

BRIEF SUMMARY OF THE INVENTION

The present invention is of an apparatus for management of fecal incontinence, comprising: means for blocking passage of stool from a rectal vault by use of an inflatable balloon; means for detecting an electrically conductive path that occurs between at least two electrodes when they come into contact with fecal matter; a non-conductive sleeve surrounding the electrodes; and means for alarming a user or caregiver upon detection of the electrically conductive path, thereby alerting the user or caregiver of a need to evacuate the rectal vault.

The present invention is also of an apparatus for management of fecal incontinence comprising a catheter having at least two electrodes and an inflatable balloon, a non-conductive sleeve surrounding the electrodes, and an alarm box, wherein the catheter is insertable into a rectal vault and is inflatable to serve as a block to passage of stool and wherein moisture sensed by the electrodes triggers the alarm box and thereby notifies a user that fecal material has entered the rectal vault. In the preferred embodiment, an integrated circuit (preferably with a memory device) is built into the catheter, the integrated circuit providing a means to monitor an amount of time that the catheter is in use. A moisture trace across the electrodes completes a voltage divider and causes a comparator to change states. The non-conductive sleeve is porous but impedes intrusion of moisture onto the electrodes, thereby allowing sensitivity of the alarming means to be tailored to different stool consistencies and reducing occurrences of false alarms during insertion. The sleeve is preferably detachable and designed for one time use, and comprises an external support flange with flexible attachment guides configured so that when the balloon is inflated, the attachment guides deform, causing the external support flange and the balloon to move closer to each other and serving to seat the balloon at an anorectal line, most preferably wherein the external support flange provides a platform onto which an absorbent pad may be added, thereby ensuring that seepage around the balloon is reduced to reduce soiling of undergarments. In one embodiment, the balloon deflates over a period of time to enforce a minimum level of attention.

The present invention is further of a method for management of fecal incontinence, comprising: blocking passage of stool from a rectal vault by use of an inflatable balloon, detecting an electrically conductive path that occurs between at least two electrodes when they come into contact with fecal matter; employing a non-conductive sleeve surrounding the electrodes; and alarming a user or caregiver upon detection of the electrically conductive path, thereby alerting the user or caregiver of a need to evacuate the rectal vault. In the preferred embodiment, the blocking, detecting, and employing steps are performed by a catheter. The method preferably additionally comprises monitoring an amount of time that the catheter is in use, most preferably employing an integrated circuit comprising a memory device. In the detecting step a moisture trace across the electrodes completes a voltage divider and causes a comparator to change states. The non-conductive sleeve is porous but impedes intrusion of moisture onto the electrodes, thereby allowing sensitivity of alarming to be tailored to different stool consistencies and reducing occurrences of false alarms during insertion. Preferably the sleeve is detachable and designed for one time use, and comprises an external support flange with flexible attachment guides configured so that when the balloon is inflated, the attachment guides deform, causing the external support flange and the balloon to move closer to each other and serving to seat the balloon at an anorectal line, most preferably wherein the external support flange provides a platform onto which an absorbent pad may be added, thereby ensuring that seepage around the balloon is reduced to reduce soiling of undergarments. In one embodiment, the method additionally comprises permitting the balloon to deflate over a period of time to enforce a minimum level of attention.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 2 is a diagram of the assembly as inserted into a subject;

FIG. 4 is a diagram of the preferred catheter tip and sleeve of the invention; and FIG. 5 is a diagram of an alternate sleeve according to the invention.

LIST OF REFERENCE NUMERALS

Figure 1:
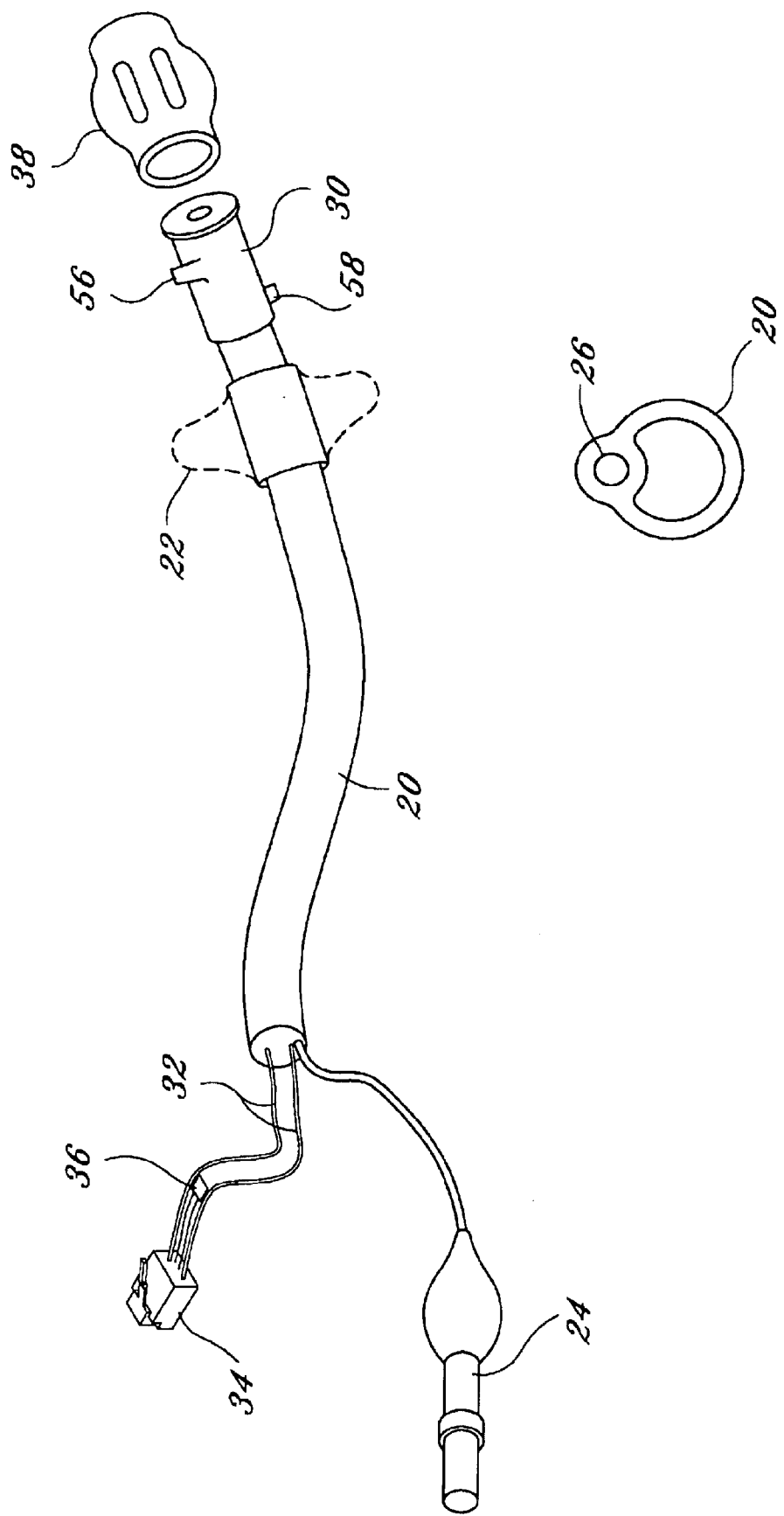
FIG. 1 is a diagram of the preferred catheter assembly of the invention.

20—Dual lumen tube
22—Balloon
24—Valve
26—Small lumen
30—Tip assembly
32—Electrical conductors
34—Electrical connector
35—Electrical connector
36—Integrated circuit
38—Sleeve assembly
39—Sleeve holes
40—Rectum
42—Stool
44—Anorectal line
46—Comparator
48—Resistor divider
50—Reference resistor
52—Comparator output
54—Patient notification device
55—Microcontroller
56—First electrode
58—Second electrode
60—Thread
62—Flatus vent hole
64—External support flange
66—Flexible attachment guides
68—Tip covering

DETAILED DESCRIPTION OF THE INVENTION

The present invention is an apparatus and method for managing fecal incontinence. The invention comprises use of a dual lumen catheter with a balloon attached near the distal end. The distal end of the catheter is inserted into the anus in a deflated condition and once resident in the rectum it is inflated to a size that blocks the passage of stool, serving the same function as the sphincter. In the tip of the catheter are two electrodes. When a moisture path is in place across these electrodes (indicative of feces impinging onto the sensor) an electrical conduction takes place that can be sensed in an attached alarm unit, thereby alerting the user to the need to evacuate the bowels. Since the electrodes are easily cleaned, the catheter may be reused multiple times. For ambulatory patients, the mechanical barrier created by the inflated balloon allows the user sufficient time to reach a toilet, thus precluding an unintended passage of stool. Voluntary evacuation is accomplished after deflating the balloon and removing the catheter from the rectum. Once the rectum is emptied, the catheter is reinserted and the balloon is reinflated.

In some embodiments, it will be desirable to use a 'leaky' balloon wherein either a calibrated leak is built into the valve assembly that is used to inflate the balloon, or the balloon itself is built of a slightly porous material through which the inflation medium passes out gradually over time. The purpose of this is to ensure that the device is not misused by leaving it unattended for extended periods of time. A balloon that repeatably and reliably deflates to an unusable small size over a period of, perhaps, four hours, ensures that the device will receive periodic attention from the user or caregiver.

The proximal end of the catheter assembly, which remains outside of the body, has a built-in integrated circuit that keeps count of the amount of time that the catheter is hooked into an alarm box. This alarm box or "patient notification device" is worn outside of the body and contains a battery and a microcontroller to process data and to signal status via audible, visual or vibrational means. Since the catheter maintains its own counter, an expiration date can be enforced, thereby ensuring that the patient does not wear the catheter for too long at a time or reuse it for too many days.

In some embodiments, the inserted tip of the catheter will have a detachable sleeve assembly that may be discarded after each use. The sleeve has four functions. First, it allows the venting of flatus through the center of the catheter without allowing the intrusion of moisture. Second, it prevents nuisance tripping when the catheter is first inserted, and during use, by preventing moisture contact with the electrodes. Different sleeve designs may be used for different patients in order to enhance fit and comfort, and/or in order to accommodate different stool consistencies. Third, in some embodiments, the sleeve facilitates insertion and positioning. Finally, in some embodiments, the sleeve itself can serve to block the passage of fecal material, thereby preventing the soilage of clothing or bed linens that could occur due to seepage around the catheter.

Making use of a relatively low cost, disposable sleeve is desirable because that is the portion of the catheter that is soiled with each use, and it is convenient to discard it with each use while retaining the more costly catheter assembly for multiple uses. In some embodiments, the sleeve itself might be incorporated into the catheter assembly with the entire assembly being cleaned after each use or with the entire catheter-sleeve assembly being discarded after each use.

FIG. 1 depicts the catheter assembly consisting of a dual lumen tube 20 to which a balloon 22 is attached on the distal end and to which a valve 24 is attached on the proximal end. The small lumen 26 within the tube 20 acts as the channel by which the balloon 22 may be inflated and deflated. By attaching a syringe or pump to the valve 24, air or another fluid may be forced into/removed from the balloon 22. Two or more electrical conductors 32 also exit the tube 20 at the proximal end. These conductors 32 connect to electrodes 56,58 that are placed in the tip assembly 30 of the catheter. These conductors 32 connect to an electrical connector 34. The electrical connector 34 will plug into an externally worn Patient Notification Device (not shown). Also attached to the electrical connector 34 are the leads from an integrated circuit 36.

Although it is feasible to fill the balloon 22 with a liquid such as saline or distilled water, when this is done, the weight of the balloon will press upon nerves surrounding the sphincter muscle and will be uncomfortable for many patients. Accordingly, the balloon 22 will generally be filled by air. Air is readily available and a balloon leak does not present serious problems. In many applications, it will be desirable to implement a slow leak that serves to deflate the balloon over time. This is to force the user or caregiver to attend to the catheter on a periodic basis and to not leave the device in situ for extended periods of time. A leak can be implemented through a pinhole in the valve 24, or by using a special material for the balloon that diffuses air over time. For example, a silicone balloon with a deflated length of 1 inch, a deflated diameter of 0.5 inches, and a wall thickness of 0.020 inches, will attain a diameter of one inch with the injection of 22 cc of air. After two hours, this diameter will be reduced to 0.7 inches due to the diffusion of air through the balloon walls.

Over the tip 30 is fitted a detachable sleeve assembly 38. This assembly serves to shield the electrodes 56,58 from direct contact with the lining of the rectum. The sleeve assembly 38 has slots through which fecal matter may enter in such a way as to electrically bridge the electrodes 56,58, causing minute electrical current leakages which are detected by a patient notification device and used to signal an alarm.

FIG. 2 depicts the device as inserted into a subject. The balloon 22 on the catheter inflates to approximately 20 cc, which is a similar volume to that used with a conventional urinary catheter. In normal use, a catheter with a deflated balloon is inserted into the rectum into a position inside of the anorectal fine 44. It is then inflated. The present invention serves to augment normal bowel function. Normal bowel function is controlled by three things: anal sphincter pressure, rectal storage capacity and rectal sensation. For a continent individual, the anal sphincter muscle contracts to prevent stool from leaving the rectum. Rectal storage occurs when the rectum 40 stretches to hold stool. This storage can continue for some time after a person becomes aware that the stool is present, allowing the person to void the stool at a convenient time and place. Rectal sensation tells the person that the stool is in the rectum 40. The device of the present invention is targeted at subjects who are unable to retain stool and/or unable to sense its presence. The balloon 22, assists the sphincter to prevent stool from exiting the rectum. Moisture from fecal matter that penetrates the sleeve assembly 38 is sensed, and this information is used to signal to the user or caregiver that fecal matter has entered the rectal vault and needs attention. Accordingly, the balloon 22 assists the sphincter in retaining stool and the sensors/alarming serves as sensation.

Figure 3:
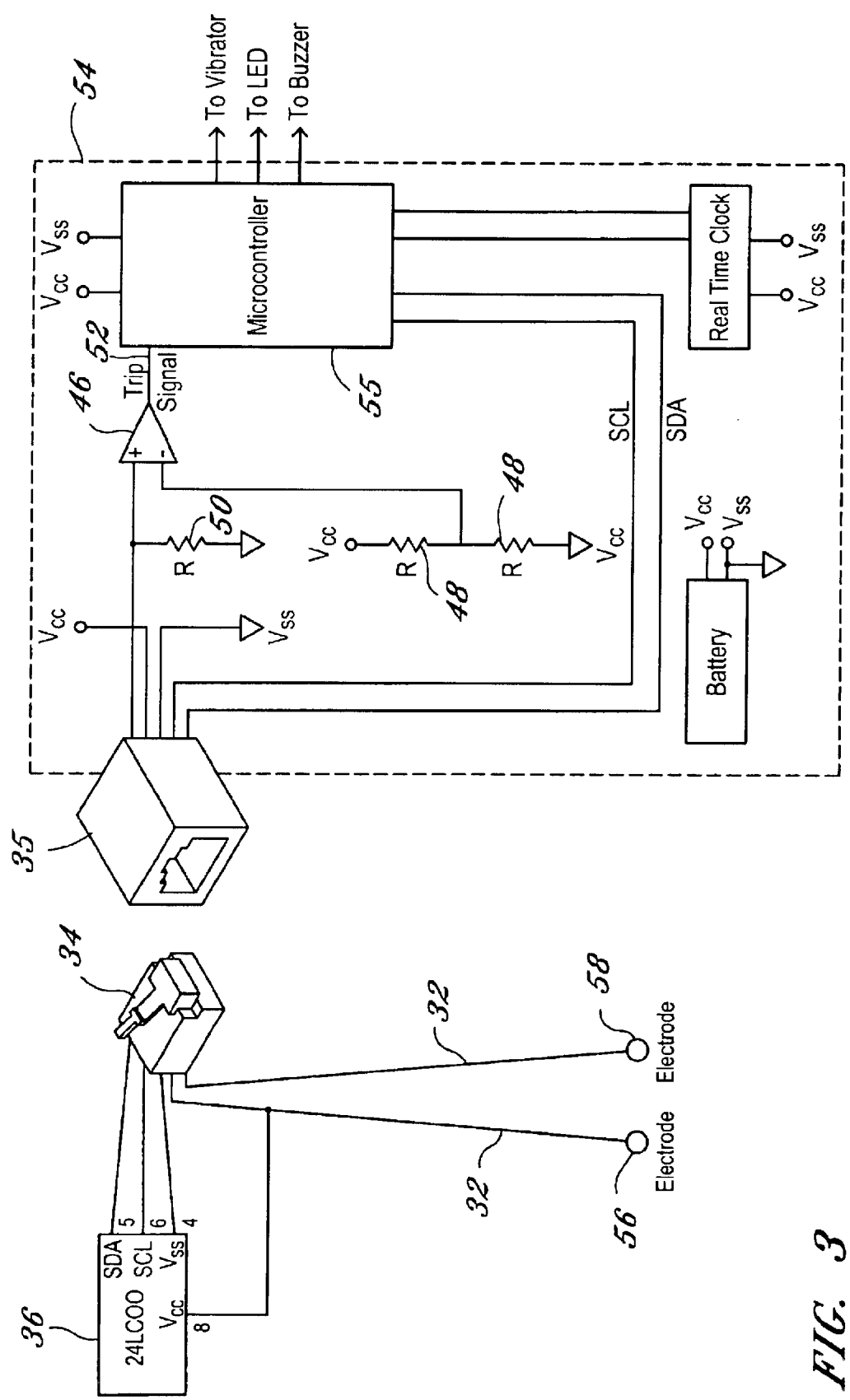
FIG. 3 is an electrical schematic of the assembly as connected to conditioning electronics within a patient notification device.

FIG. 3 depicts an electrical schematic of the catheter assembly as it is connected to conditioning electronics within a Patient Notification Device 54. Two electrodes 56,58 are connected through electrical conductors 32 to form the top leg of a voltage divider that feeds into the noninverting input of a comparator 46. When there is an open circuit across the electrodes 56,58, the reference resistor 50 serves to ground the noninverting input of the comparator 46. This causes the output 52 to be at a zero potential. The resistor divider 48 is formed from equal resistances and creates a reference point for the electrodes 56,58. When a moisture path creates a resistance across electrodes 56,58 that is less than the reference resistor 50, the output 52 of the comparator 46 assumes a positive potential that is sensed by the microcontroller 55. The microcontroller 55 can then trigger an audible alarm, vibrator and/or visual indicator in response.

FIG. 3 depicts one possible electrical configuration for the electrodes 56,58 and the integrated circuit 36, as it would be implemented to reside in the catheter. The integrated circuit 36 that is depicted is a type 24LC00 serial EEPROM which is manufactured by Microchip Technology Inc. This integrated circuit is a memory device and has 16 bytes of read/write memory that is accessed serially. The memory is nonvolatile and electrically erasable. Each memory location is accessed serially using the SCL (serial clock) and SDA (serial data) lines. The integrated circuit 36 attaches to a connector 34. This connector could be any standard connector having five or more low voltage wires. For example, a standard RJ45 telephone jack with six conductors would be suitable. When the connector 34 is inserted into a patient notification device, power is applied to integrated circuit 36 via the lines Vcc and Vss. Prior to shipment to the end user, the integrated circuit 36 will be programmed with relevant information. This relevant information could include a serial number, date of manufacture, expiration date, total elapsed minutes of operation allowed, or other information. When the integrated circuit 36 is connected to the Patient Notification Device (PND) 54, the PND 54 continuously monitors the state of the electrodes to see if fecal bridging across the electrodes 56 and 58 has occurred. In addition, periodically (for the sake of this discussion, once per minute), the PND 54 reads the memory in integrated circuit 36, decrements the minute counter and reprograms the integrated circuit 54 with the new minute count. If the minute count reaches zero, then the patient notification device 54 notifies the user, via a blinking light or other indicator, that the catheter needs to be replaced. The Patient Notification Device (PND) 54 also reads the expiration date that is stored in the integrated circuit 54 and checks it against the current date to see if the catheter has expired. The unique serial number stored within the catheter allows a means to identify product and manufacturing date in the case of recalls or audit.

The Patient Notification Device has the size and appearance of a conventional pager. Like a pager, it can be worn on a belt or clipped to the clothes. Like a pager, it can notify the user or caregiver by means of either an audible alarm or a vibration. The PND is battery powered. It interfaces to the electrodes. 56,58 at the distal end of the catheter and senses a conductive path (due to moisture) that occurs between the electrodes. It serves to amplify and/or filter this signal to generate an alarm signal upon the occurrence of feces being forced into the sleeve and bridging the electrodes. The PND has an internal microcontroller and real time clock. During the entire time that a catheter is attached to the PND, at one minute intervals (or other appropriate intervals), the PND will update the counter in the catheter with a minute (or other appropriate) count. Alternatively, for some implementations, the PND might decrement a minute counter in the catheter. Additionally, in some implementations, the PND might read an expiration date from the catheter and check this against the present date in order to determine if the catheter is too old. The point of this is to ascribe an expiration date to the catheter and/or a maximum usable time frame. When the catheter is close to the expiration date or is reaching the end of its usable life, the PND might sound an audible alarm or flash an LED or otherwise indicate that the catheter needed to be discarded in favor of a new catheter. One other possible feature of the PND would be to sound an alarm if the catheter has not been removed in two hours, three hours or some arbitrary time interval, in order to ensure that the catheter receives regular maintenance and attention and to minimize the possibility for adverse events such as fecal impaction or necrosis of tissues lining the rectal vault.

FIG. 4 depicts a detail of the catheter tip 30 and sleeve 38. Whereas the catheter body is a soft tube made of silicone or a similar biologically inert, pliable substance, the tip is relatively rigid and in some embodiments may be hollow in order to accommodate the venting of flatus. The Up 30 has a ridge (or thread) onto which a threaded sleeve may be screwed. The sleeve 38 is preferably injection molded out of a soft, biologically inert material and, in some embodiments, will have a flatus venting hole 62 that is plugged with a material that is porous to gas but blocks the intrusion of solids or liquids. Although in its preferred embodiment, the sleeve 38 is designed to be detachable from the catheter and disposable, it might be permanently affixed to the catheter, and/or it might be designed for multiple use.

The sleeve 38 over the electrodes 56,58 operates to prevent nuisance tripping. The sleeve design influences the speed with which stool impinges upon the electrodes 56,58, causing a fecal detection event. If the holes 39 in the sleeve are large, there is little resistance and this style of sleeve might be appropriate for patients with firm stool. Small holes offer more resistance and are preferable for soft or watery stool.

The sleeve 38 in fact can have at least five functions. First, it allows the venting of flatus through the center of the catheter without allowing the intrusion of moisture. Second, it prevents nuisance tripping when the catheter is first inserted into the rectum, and during use, by impeding moisture contact with the electrodes 56,58. Third, different sleeve designs may be used for different patients in order to enhance fit and comfort, and/or in order to accommodate different stool consistencies. Fourth, in some embodiments, the sleeve 38 facilitates insertion and positioning. Finally, in some embodiments, the sleeve 38 itself can serve to block the passage of fecal material, thereby preventing the soilage of clothing or bed linens that could occur due to seepage around the inflated catheter.

FIG. 5 depicts a modified sleeve design that includes an external support flange 64. Flexible attachment guides 66 connect between the tip covering 68 and the support flange 64. When the sleeve design is installed over a catheter, the flexible attachment guides 66 will deform when the balloon is inflated, allowing for an automatic seating of the inflated balloon at the anorectal line and thereby blocking the unwanted leakage of stool by means of the inflated balloon. In addition, the support flange 64 provides a platform to which may be added an absorbent pad which can ensure that any seepage around the balloon is controlled and does not soil undergarments.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for management of fecal incontinence, said apparatus comprising:
   means for blocking passage of stool from a rectal vault by use of an inflatable balloon;
   means for detecting an electrically conductive path that occurs between at least two electrodes when they come into contact with fecal matter;
   non-conductive sleeve surrounding said electrodes; and
   means for alarming a user or caregiver upon detection of said electrically conductive path, thereby alerting the user or caregiver of a need to evacuate the rectal vault; and
   wherein a moisture trace across said electrodes completes a voltage divider and causes a comparator to change states.

2. An apparatus for management of fecal incontinence comprising a catheter having at least two electrodes and an inflatable balloon, a non-conductive sleeve surrounding said electrodes, and an alarm box, wherein the catheter is insertable into a rectal vault and is inflatable to serve as a block to passage of stool and wherein moisture sensed by said electrodes triggers said alarm box and thereby notifies a user that fecal material has entered the rectal vault, and wherein a moisture trace across said electrodes completes a voltage divider and causes a comparator to change states.

3. The apparatus of claim 2 wherein an integrated circuit is built into said catheter, said integrated circuit providing a means to monitor an amount of time that the catheter is in use.

4. The apparatus of claim 3 wherein said integrated circuit comprises a memory device.

5. The apparatus of claim 2 wherein said non-conductive sleeve is porous but impedes intrusion of moisture onto said electrodes, thereby allowing sensitivity of said alarming means to be tailored to different stool consistencies and reducing occurrences of false alarms during insertion.

6. The apparatus of claim 5 wherein said sleeve is detachable and designed for one time use.

7. The apparatus of claim 5 wherein said sleeve comprises an external support flange with flexible attachment guides configured so that when said balloon is inflated, said attachment guides deform, causing said external support flange and said balloon to move closer to each other and serving to seat said balloon at an anorectal line.

8. The apparatus of claim 7 wherein said external support flange provides a platform onto which an absorbent pad may be added, thereby ensuring that seepage around the balloon is reduced to reduce soiling of undergarments.

9. The apparatus of claim 2 wherein said balloon deflates over a period of time to enforce a minimum level of attention.

10. A method for management of fecal incontinence, the method comprising the steps of:
    blocking passage of stool from a rectal vault by use of an inflatable balloon;
    detecting an electrically conductive path that occurs between at least two electrodes when they come into contact with fecal matter;
    employing a non-conductive sleeve surrounding the electrodes; and
    alarming a user or caregiver upon detection of the electrically conductive path, thereby alerting the user or caregiver of a need to evacuate the rectal vault; and
    wherein in the detecting step a moisture trace across the electrodes completes a voltage divider and causes a comparator to change states.

11. The method of claim 10 wherein the blocking, detecting, and employing steps are performed by a catheter.

12. The method of claim 11 additionally comprising the step of monitoring an amount of time that the catheter is in use.

13. The method of claim 12 wherein the monitoring step employs an integrated circuit comprising a memory device.

14. The method of claim 10 wherein in the employing step the non-conductive sleeve is porous but impedes intrusion of moisture onto the electrodes, thereby allowing sensitivity of alarming to be tailored to different stool consistencies and reducing occurrences of false alarms during insertion.

15. The method of claim 14 wherein the sleeve is detachable and designed for one time use.

16. The method of claim 14 wherein the sleeve comprises an external support flange with flexible attachment guides configured so that when the balloon is inflated, the attachment guides deform, causing the external support flange and the balloon to move closer to each other and serving to seat the balloon at an anorectal line.

17. The method of claim 16 wherein the external support flange provides a platform onto which an absorbent pad may be added, thereby ensuring that seepage around the balloon is reduced to reduce soiling of undergarments.

18. The method of claim 10 additionally comprising the step of permitting the balloon to deflate over a period of time to enforce a minimum level of attention.

19. An apparatus for management of fecal incontinence comprising a catheter having at least two electrodes and an inflatable balloon, a non-conductive sleeve surrounding said electrodes, and an alarm box, wherein the catheter is insertable into a rectal vault and is inflatable to serve as a block to passage of stool and wherein moisture sensed by said electrodes triggers said alarm box and thereby notifies a user that fecal material has entered the rectal vault, and wherein an integrated circuit is built into said catheter, said integrated circuit providing a means to monitor an amount of time that the catheter is in use.

20. The apparatus of claim 19 wherein said integrated circuit comprises a memory device.

21. An apparatus for management of fecal incontinence comprising a catheter having at least two electrodes and an inflatable balloon, a non-conductive sleeve surrounding said electrodes, and an alarm box, wherein the catheter is insertable into a rectal vault and is inflatable to serve as a block to passage of stool and wherein moisture sensed by said electrodes triggers said alarm box and thereby notifies a user that fecal material has entered the rectal vault, wherein said non-conductive sleeve is porous but impedes intrusion of moisture onto said electrodes, thereby allowing sensitivity of said alarming means to be tailored to different stool consistencies and reducing occurrences of false alarms during insertion, and wherein said sleeve comprises an external support flange with flexible attachment guides configured so that when said balloon is inflated, said attachment guides deform, causing said external support flange and said balloon to move closer to each other and serving to seat said balloon at an anorectal line.

22. The apparatus of claim 21 wherein said external support flange provides a platform onto which an absorbent pad may be added, thereby ensuring that seepage around the balloon is reduced to reduce soiling of undergarments.

23. A method for management of fecal incontinence, the method comprising the steps of:
    blocking passage of stool from a rectal vault by use of an inflatable balloon;
    detecting an electrically conductive path that occurs between at least two electrodes when they come into contact with fecal matter;

employing a non-conductive sleeve surrounding the electrodes;

alarming a user or caregiver upon detection of the electrically conductive path, thereby alerting the user or caregiver of a need to evacuate the rectal vault; and monitoring an amount of time that the catheter is in use.

24. The method of claim 23 wherein the monitoring step employs an integrated circuit comprising a memory device.

25. A method for management of fecal incontinence, the method comprising the steps of:

blocking passage of stool from a rectal vault by use of an inflatable balloon;

detecting an electrically conductive path that occurs between at least two electrodes when they come into contact with fecal matter;

employing a non-conductive sleeve surrounding the electrodes; and alarming a user or caregiver upon detection of the electrically conductive path, thereby alerting the user or caregiver of a need to evacuate the rectal vault; and wherein in the employing step the non-conductive sleeve is porous but impedes intrusion of moisture onto the electrodes, thereby allowing sensitivity of alarming to be tailored to different stool consistencies and reducing occurrences of false alarms during insertion; and wherein the sleeve comprises an external support flange with flexible attachment guides configured so that when the balloon is inflated, the attachment guides deform, causing the external support flange and the balloon to move closer to each other and serving to seat the balloon at an anorectal line.

26. The method of claim 25 wherein the external support flange provides a platform onto which an absorbent pad may be added, thereby ensuring that seepage around the balloon is reduced to reduce soiling of undergarments.

* * * * *